Aug. 5, 1975
F. W. ANDERSON
Plant Pat. 3,758
DWARF NECTARINE TREE
Filed Sept. 23, 1974
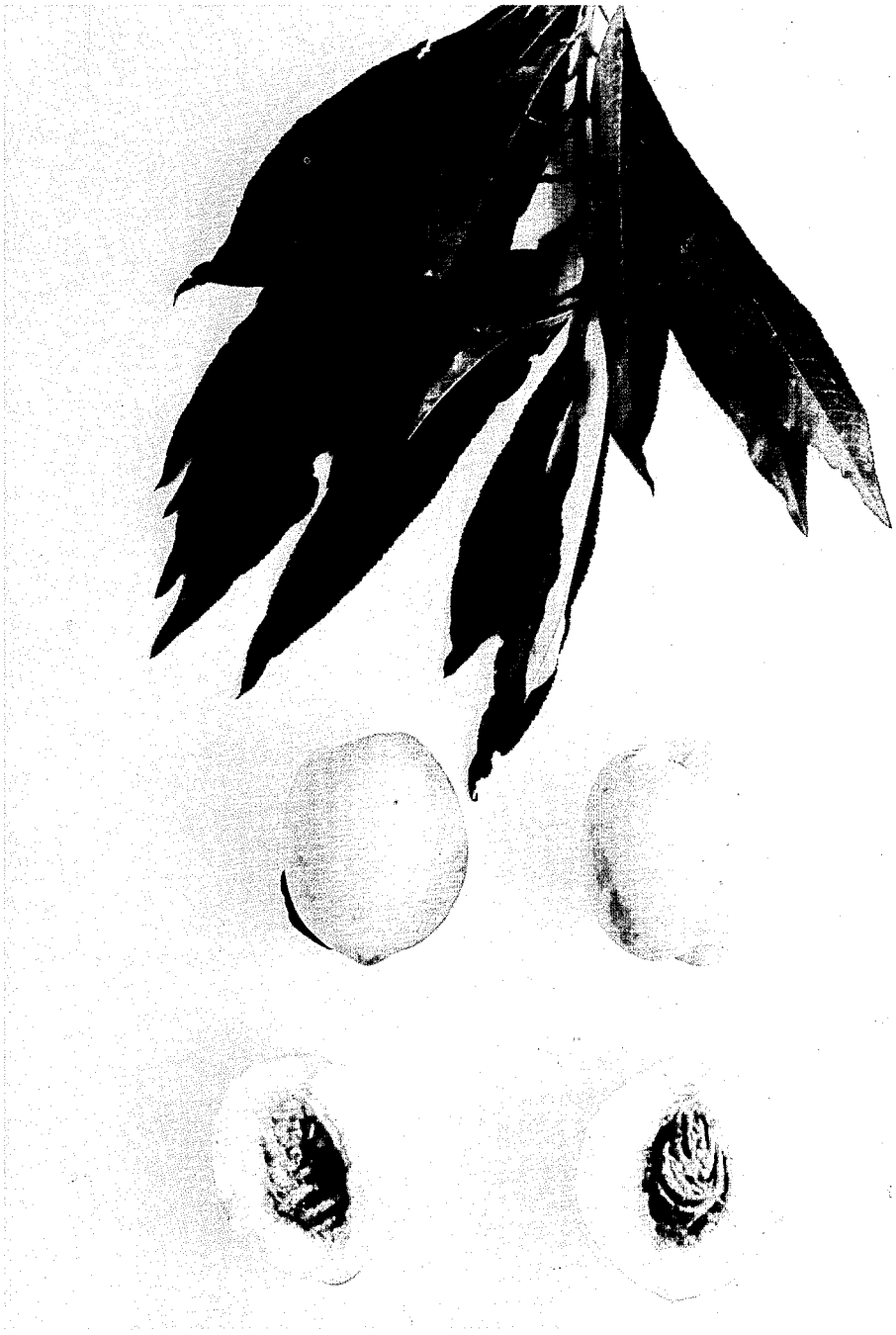

United States Patent

Plant Pat. 3,758
Patented Aug. 5, 1975

3,758

DWARF NECTARINE TREE

Frederic W. Anderson, Merced, Calif., assignor to L. E. Cooke Co., Visalia, Calif.

Filed Sept. 23, 1974, Ser. No. 508,700
Int. Cl. A01h 5/03
U.S. Cl. Plt.—41 1 Claim

ABSTRACT OF THE DISCLOSURE

A brachytic dwarf nectarine tree which is of medium size, spreading, dense, foliated with large, lanceolate, acutely pointed leaves having a crenate margin and short petiole, and a regular and productive bearer of large, oblong, freestone fruit, variable both as to size and form, having yellow skin partially overspread with red, yellow flesh, and a red pit cavity from which the red streaks slightly into the flesh.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of dwarf nectarine tree resulted from my endeavors in the conduct of such plant breeding program.

ORIGIN OF THE VARIETY

The present variety of dwarf nectarine tree was originated by me, in my experimental nursery and orchard located as aforesaid, as a cross between the Empress dwarf peach (U.S. Plant Pat. No. 2,533) and the Bonanza dwarf peach (U.S. Plant Pat. No. 2,213) $F_2$.

ASEXUAL REPRODUCTION OF THE VARIETY

The present variety of dwarf nectarine tree was, upon recognition by me of its new and distinct characteristics, asexually reproduced by me by top-working on orchard trees in my said orchard, and—in maturity—such asexual reproductions ran true to the original tree, and its fruit, in all respects.

SUMMARY OF THE VARIETY

The present variety of brachytic dwarf nectarine tree is of medium size, spreading, dense, foliated with large, lanceolate, acutely pointed leaves having a crenate margin and short petiole, and a regular and productive bearer of large, oblong, freestone fruit, variable both as to size and form, having yellow skin partially overspread with red, yellow flesh, and a red pit cavity from which the red streaks slightly into the flesh; the fruit, as best compared with that of the Sunburst nectarine (U.S. Plant Pat. No. 3,330), being freestone rather than clingstone, larger, more tender in flesh texture, and ripens about two weeks later.

BRIEF DESCRIPTION OF THE DRAWING

The drawing is an illustration, by photographic reproduction in color, of a twig with leaves, and separate fruit; one of the fruit being cut in half to expose the flesh, with the stone remaining in one half.

DESCRIPTION OF THE VARIETY

The botanical details of this new and distinct variety of dwarf nectarine tree—with color definitions (except those in common color terms) referenced to Maerz and Paul Dictionary of Color—are as follows:

TREE
- *Class.*—Brachytic dwarf.
- *Size.*—Medium.

- *Vigor.*—Medium.
- *Growth.*—Spreading.
- *Density.*—Dense.
- *Production.*—Productive.
- *Bearing.*—Regular bearer.

TRUNK
- *Size.*—Medium.

BRANCHES
- *Size.*—Stocky.
- *Texture.*—Medium.
- *Color.*—Green.

LEAVES
- *Size.*—Large. Average length—8½". Average width—1⅜".
- *Form.*—Lanceolate. Acutely pointed.
- *Thickness.*—Medium.
- *Margin.*—Crenate.
- *Petiole.*—Short. Medium thickness.
- *Glands.*—Average number—2. Alternate. Medium size. Reniform. Usually positioned on base of blade.
- *Color.*—Top side—Medium green (23–L–8). Under side—Lighter green (22–L–7).

FLOWERS
- *Blooming period.*—March 1 to March 15, 1974. Early to medium, as compared with other varieties.
- *Size.*—Large.

FRUIT
- *Maturity when described.*—Overripe—Aug. 15, 1974.
- *Date of first picking.*—Aug. 1, 1974.
- *Date of last picking.*—Aug. 15, 1974.
- *Size.*—Variable. Large. Average diameter axially—2⅝". Average transversely in suture plane—2⅜".
- *Form.*—Variable. Oblong.
- *Suture.*—Shallow.
- *Ventral surface.*—Rounded slightly.
- *Cavity.*—Average depth—½". Average breadth—¾".
- *Apex.*—Short.

SKIN
- *Thickness.*—Thin.
- *Texture.*—Tender.
- *Tendency to crack.*—None noted.
- *Color.*—Yellow (10–L–5) partially overspread with red (6–L–5).

FLESH
- *Juice.*—Moderate.
- *Texture.*—Soft. Melting.
- *Aroma.*—Distinct.
- *Eating quality.*—Fair to good.
- *Color.*—Yellow (10–L–6). Surface of pit cavity: Red, with red streaked slightly into flesh.

STONE
- *Type.*—Free.
- *Size.*—Medium. Average length—1½". Average breadth—1". Average thickness—⅝".
- *Form.*—Obovoid.
- *Apex.*—Acute.
- *Sides.*—Equal.
- *Tendency to split.*—Slight.
- *Color.*—Brown (8–J–11).

USE
- *Market.*—local.

KEEPING QUALITY
- Medium.

RESISTANCE TO INSECTS AND DISEASES
- No usual suscpetibilities noted.

SHIPPING QUALITY
- Medium.

The dwarf nectarine tree and its fruit herein described may vary in slight detail due to climatic and soil conditions under which the variety may be grown; the present description being of the variety as grown in the Central Valley of California.

I claim:

1. A new and distinct variety of brachytic dwarf nectarine tree, substantially as illustrated and described, which is of medium size, spreading, dense, foliated wtih large, lanceolate, acutely pointed leaves having a crenate margin and short petiole, and a regular and productive bearer of large, oblong, freestone fruit, variable both as to size and form, having yellow skin partially overspread with red, yellow flesh, and a red pit cavity from which the red streaks slightly into the flesh; the fruit, as best compared with that of the Sunburst nectarine, being freestone rather than clingstone, larger, more tender in flesh texture, and ripens about two weeks later.

No references cited.

ROBERT E. BAGWILL, Primary Examiner